United States Patent [19]

Kan

[11] 4,324,861
[45] Apr. 13, 1982

[54] PREPARATION OF LIVE ATTENUATED MUMPS VIRUS FOR A VACCINE

[75] Inventor: Takayoshi Kan, Kanonji, Japan

[73] Assignee: Research Foundation for Microbial Diseases of Osaka University, Osaka, Japan

[21] Appl. No.: 100,957

[22] Filed: Dec. 6, 1979

[30] Foreign Application Priority Data

May 4, 1979 [JP] Japan ................................ 54-055094

[51] Int. Cl.$^3$ .............................................. C12N 7/08
[52] U.S. Cl. ...................................... 435/237; 424/89
[58] Field of Search ........................... 435/237; 424/89

[56] References Cited

U.S. PATENT DOCUMENTS 3,555,149  1/1971  Buynak et al. ........................ 424/89
3,961,046  6/1976  Cerini ................................... 435/237
4,071,618  1/1978  Konobe et al. ....................... 424/89

OTHER PUBLICATIONS

Purchase et al.-Amer. J. Vet. Research, vol. 32, No. 11 (Nov. 1971), pp. 1811-1823.
Horta-Barbosa et al.-Applied Microbiology, vol. 18, No. 2 (1969), pp. 251-255.

Primary Examiner—Sam Rosen
Attorney, Agent, or Firm—Armstrong, Nikaido, Marmelstein & Kubovcik

[57] ABSTRACT

A live attenuated mumps virus vaccine is prepared by cultivating a wild mumps virus strain for 1-18 serial passages in a first living cell to attenuate the virus, and then cultivating the attenuated virus in a second living cell for at least one serial passage to propagate and adapt the virus to the cell. The cell is selected from embryonated hen's egg amnion, embryonated hen's egg chorio-allantoic membrane, chick embryo fibroblast and human diploid cell. Quail embryo fibroblast is also employed. The vaccine prepared has strong immunogenecity and is safe.

8 Claims, No Drawings

PREPARATION OF LIVE ATTENUATED MUMPS VIRUS FOR A VACCINE

BACKGROUND OF THE INVENTION

This invention relates to a novel process for preparing a live attenuated mumps virus vaccine which is effective for preventing epidemic parotitis (to be referred to as "mumps", hereinafter) infection.

Mumps is so contagious that kindergartens and primary schools are often closed during the prevalence thereof. Since those infected with mumps usually recover their health relatively quickly, mumps is considered a mild disease. However, since it is found that adults infected with mumps are attacked at testicle or ovary organs and as a result, become sterile, vaccines for preventing mumps infection are needed. Both live vaccine and inactivated vaccine had been investigated, but since inactivated vaccine cannot bring immunity lasting for a sufficient time after administration, it is now almost out of date. Live vaccine expected of prolonged immunity is now regarded feasible and a number of researches have been made on the preparation of live mumps virus vaccine. Exemplary of the culture host for mumps virus are amnion and chorio-allantoic membranes of embryonated hens' eggs and chicken embryo fibroblast cells. The article of Enders et al., Journal of Immunology, Vol. 54, 283–291 (1946) discloses the use of amniotic membranes which are ground and centrifuged. Only the pathogenicity of the virus for the monkey is indicated. The article of Henle et al., Journal of Immunology, Vol. 66, 579–594 (1951) discloses the virus of several allantoic passages. Smorodintsev et al. describes in Acta virol, 9, 240–247, (1965) that mumps virus is propagated in cultures of chicken embryo cells. However, no live vaccine has been prepared according to the teachings mentioned above. One live attenuated vaccine which has been used in practice is a live attenuated vaccine of Jeryl Lynn strain (see for example, The New England Journal of Medicine, Vol. 276, No. 5, 245–258 (1967)). Such live vaccines have several disadvantages in that the resultant antibody titre in blood is considerably lower than in the case of natural infection, the immunity may be retained for only a short time, and serial passage often attenuates the virus to an undesirable low level.

Therefore, vaccine having a high antibody production capacity is desired. Mumps virus generally tends to be relatively readily adapted and its immunogenecity tends to diminish rapidly. Factors of attenuation and immunogenecity retention thus appear to be alternative. Therefore, it is necessary to provide a process for the preparation of a live attenuated vaccine which is properly attenuated and retains continuing immunogenicity.

SUMMARY OF THE INVENTION

The inventor has found that the above object can be attained by subjecting a newly isolated wild mumps virus strain, "URABE strain", to attenuation, adaptation and propagation in avian cells and/or human diploid cells.

The avian cells used herein are amnions and chorioallantoic membranes of embryonated hens' eggs chicken embryo fibroblast and quail embryo fibroblast cells. The human diploid cells used herein are, for example, WI-38 strain cells and MRC-5 strain cells.

This invention comprises two steps of several virus-passages in a living cell selected from the above cells; for attenuation of a wild virulent mumps virus, and for propagation and adaptation of the resultant attenuated mumps virus to the cell in order to produce an attenuated mumps virus vaccine in high yields. A species of the living cell used in each of the above steps is permitted to be identical with or different from each other.

According to this invention, the culture host for attenuating wild virulent mumps virus and the culture host for propagating the attenuated virus may be of the same species or of different species. Preferably, amnions of embryonated hens' eggs may be used for the attenuation of a wild strain and in combination with this, amnions of embryonated hens' eggs, quail embryo fibroblast cells and human diploid cells may be used for the propagation stage.

Illustratively, mumps virus is inoculated in a living cell and incubated at 32°–39° C. for 3–7 days, and then the resulting culture solution is harvested. Under such culture conditions, the mumps virus may be subject to 1–30 serial passages to obtain a live attenuated mumps virus vaccine having strong immunogenecity. Usually, the concentration of virus to be inoculated is about $10^6$ $TCID_{50}$/ml and serial passage according to this invention increases the concentration to about $10^8$ to $10^9$ $TCID_{50}$/ml. In the case of tissue culture the amount of virus to be inoculated is selected so that the multiplicity of infection (MOI) will fall within the range between 0.1 and 0.001.

In the most preferred embodiments, the culture host for attenuating wild mumps virus is embryonated hen's egg amnion and the culture host for the subsequent propagation and adaptation of the attenuated virus is embryonated hen's egg amnion, quail embryo fibroblast or human diploid cell. The virus is most preferably cultivated in egg amnions for 5–6 days after inoculating the virus into an amniotic cavity, and the cultivated virus is collected from the amniotic fluid which can be harvested aseptically.

DESCRIPTION OF THE PREFERRED EMBODIMENTS

The invention will be more fully understood with reference to the following Examples.

EXAMPLE 1

A wild strain of virulent mumps virus was isolated and then inoculated into the amniotic cavity of 7-day-old embryonated eggs of hens belonging to an SPF (specific pathogen free) flock of hens bred in a vinyl isolator. The virus was cultivated at 34°–36° C. for 5–6 days. Thereafter, the amniotic fluid was harvested as a mumps virus fluid. Similar cultivation was serially repeated for 8–14 passages, obtaining an attenuated mumps virus strain.

EXAMPLE 2

A tissue culture of quail embryo fibroblast cells was prepared by aseptically taking an embryo out of an 8 to 10-day-old embryonated quail egg or SPF quails bred in a vinyl isolator. The embryo cells were trypsinized in a usual manner. Then, the cells were suspended in MEM (minimum essential medium) containing 5% a calf serum at a cell concentration of $1 \times 10^6$ cells/ml. A 100-ml portion of the cell suspension was poured in a 1000 ml Roux's vessel. The cells were cultivated at 37° C. for 1–3 days until growing monolayer.

A wild strain of virulent mumps virus was isolated and inoculated into the tissue culture of quail embryo fibroblast cells. The virus was cultivated at 32°–35° C. for 4–7 days. Thereafter, the culture medium was harvested as a mumps virus fluid.

The above virus fluid was centrifuged and the supernatant was employed on the next virus cultivation. Similar cultivation was serially repeated for 5–10 passages, from which an attenuated mumps virus strain was obtained.

EXAMPLE 3

A cell culture of WI-38 human diploid cells was obtained through several serial cell-passages of cultivation at intervals of 3–4 days in an Eagle's basal medium containing 10% of fetal calf serum. The WI-38 cell culture used has a serial passage number of less than 30.

A wild strain of virulent mumps virus was isolated and inoculated into this cell culture. After virus adsorption at 35°–39° C. for 1 hour, to the culture vessel was added MEM containing 3% of calf serum. The virus was cultivated at 35°–39° C. for 4–7 days. Thereafter, the culture medium was harvested as a mumps virus fluid. The virus fluid was then centrifuged and the supernatant was employed on the next virus cultivation. Similar cultivation was serially repeated for 8–18 passages, from which an attenuated mumps virus strain was obtained.

EXAMPLE 4

An 11th passage attenuated mumps virus strain which was prepared according to Example 1 was inoculated in the amniotic cavity of an embryonated hen's egg at a virus concentration of $10^6$ TCID$_{50}$/ml. The eggs inoculated were incubated at 33°–36° C. for 5–6 days. The amniotic fluid was harvested as a mumps virus fluid containing $10^9$ TCID$_{50}$/ml of the virus. The amniotic fluid harvested as such was ready for use as a vaccine.

Since an unpurified vaccine generally contains various tissue components in addition to virus particles, it is preferable to purified. The virus was purified by low speed- and ultra-centrifugation and then was suspended in a suitable medium, for example, a Dulbecco's phosphate buffered saline solution admixed with 0.5 w/v% gelatin, and a ready-for-use vaccine was obtained.

To the vaccine was further added a small amount of a stabilizer, for example, 0.5 w/v% of gelatin. The vaccine was divided into a plurality of small containers. Lyophilization resulted in dried vaccine which was stable for a prolonged period of storage.

EXAMPLE 5

An 11th passage attenuated mumps virus strain ($10^6$ TCID$_{50}$/ml) which was prepared according to Example 1 was inoculated into a tissue culture of quail embryo fibroblast cells. The virus was propagated at 33°–36° C. for 4–7 days. The culture solution was collected as a mumps virus fluid ($10^8$ TCID$_{50}$/ml). The virus was subjected to 5–10 passages of cultivation in a similar manner, thereby being adapted to quail embryo fibroblast cells. It became feasible to use a quail embryo fibroblast cell as a culture host in order to obtain an attenuated virus for vaccine in high yields. In the subsequent steps, the thus adapted virus was used as a seed.

A 10-ml portion of the virus fluid which had been diluted 100 times in volume with an Earle's solution was inoculated into quail embryo fibroblast cells growing monolayer in a 100-ml Roux's vessel. After virus adsorption at 33°–36° C. for 1 hour, the liquid contents were discarded. MEM containing 3% calf serum was introduced into the vessels in an amount of 100 ml per vessel. The vessels were incubated at 33°–36° C. for 2–3 days. For a medium change, after the culture medium was discarded, the vessels were washed twice each with 100 ml of an Earle's balanced salt solution. A fresh tissue culture medium, M-199 was introduced into the vessels in an amount of 100 ml per vessel. The virus was further cultivated at 33°–36° C. for 2–4 days. The virus fluid was centrifuged at low speed, and the supernatant was harvested as a vaccine fluid. A dried vaccine was prepared from the above vaccine fluid in the same way as described in Example 4.

EXAMPLE 6

An attenuated mumps virus strain ($5 \times 10^6$ TCID$_{50}$/ml) which was prepared for 11 passages according to Example 1 was inoculated at MOI of 0.05 into a tissue culture of WI-38 cells, which was propagated at 35°–39° C. for 4–7 days. The resulting culture medium was harvested as a mumps virus fluid. Similar cultivation was serially repeated for 7–17 passages for the purpose of adaptation of the mumps virus to WI-38 cells. It became feasible to use WI-38 as a culture host in order to obtain an attenuated virus for vaccine in high yields. In the subsequent steps, the thus adapted virus was used as a seed.

A 10-ml portion of the virus fluid which has been diluted 100 times in volume with an Earle's solution was inoculated in WI-38 cell culture having a passage number of less than 30 in a 1000ml Roux's vessel. After virus adsorption at 35°–39° C. for 1 hour, the liquid contents were discarded. Cultivation and purification of the virus was carried out as in Example 5, and the virus fluid was available as a vaccine. A dried vaccine was prepared from the above virus fluid in the same way as described in Example 4.

EXAMPLE 7

An attenuated mumps virus strain which was prepared for 11 passages according to Example 1 was inoculated into a tissue culture of MRC-5 human diploid cells. The virus was propagated at 35°–39° C. for 4–7 days. The resulting culture medium was harvested as a mumps virus liquid. Similar cultivation was serially repeated for 7–17 passages for the purpose of adaptation of the mumps virus to the MRC-5 cell. It became feasible to use the MRC-5 cell as a culture host in order to obtain an attenuated virus for vaccine in high yields. In the subsequent steps, the thus adapted virus was used as a seed.

According to the same procedure as described in Example 6, the adapted virus was cultivated in MRC-5 cell culture having a passage number of less than 30, and the virus fluid was available as a vaccine. A dried vaccine was prepared from the above virus fluid in the same way as described in Example 4.

EXAMPLE 8

An attenuated mumps virus strain which was prepared for 11 passages according to Example 1 was inoculated in the chorio-allantoic cavity of an embryonated hen's egg and was propagated at 33°–36° C. for 5–6 days. Then the allantoic fluid was harvested. Similar cultivation was serially repeated for 7–17 passages for the purpose of adaptation of the mumps virus to chorio-allantoic membranes of embryonated hens' eggs. It became feasible to use chorio-allantoic membrane of an embryonated hen's egg as a culture host to obtain an attenuated virus for vaccine in high yields. In the subsequent steps, the thus adapted virus was used as a seed.

The seed virus was inoculated in the chorio-allantoic cavity of an embryonated hen's egg and cultivated at 34°-35° C. for 5-6 days. Then the allantoic fluid was harvested. The harvested allantoic fluid was concentrated and purified as in Example 4. After addition of a suitable stabilizer, the vaccine fluid was divided into a plurality of small containers, and lyophilized for a dried vaccine.

EXAMPLE 9

An attenuated mumps virus strain which was prepared for 9 serial passages according to Example 2 was further propagated for 5-20 serial passages as in Example 1 using the amniotic cavity of an embryonated hen's egg, thereby being adapted to anmions of embryonated hens' eggs. It became possible to use an amnion of an embryonated hens' egg as a culture host to obtain an attenuated virus for vaccine in high yields. This mumps virus was used as a seed and inoculated into an amniotic cavity of an embryonated hen's egg as in Example 4 and was cultivated at 34°-36° C. The amniotic fluid was harvested, and the mumps virus was concentrated and purified. After addition of a suitable stabilizer, the vaccine solution was divided into a plurality small containers, and lyophilized for a dried vaccine.

EXAMPLE 10

An attenuated mumps virus strain which was prepared for 9 serial passages according to Example 2 was inoculated in a quail fibroblast cell as in Example 5 and cultivated at 33°-36° C. for 4-7 days. After addition of a suitable stabilizer to the culture medium centrifuged as in Example 4, the vaccine fluid was divided into a plurality of small containers, and lyophilized for a dried vaccine.

EXAMPLE 11

An attenuated mumps virus strain which was prepared for 9 serial passages according to Example 2 was propagated for 5-20 serial passages as in Example 3 using the WI-38 cell, for the purpose of adaptation of the mumps virus to WI-38 cells. It became feasible to use WI-38 cells as a culture host to obtain an attenuated virus for vaccine in high yields. This mumps virus was used as a seed and inoculated into WI-38 cells as in Example 6 and was cultivated at 35°-39° C. for 4-7 days. After addition of a suitable stabilizer to the culture medium centrifuged as in Example 4, the vaccine fluid was divided into a plurality of small containers, and lyophilized for a dried vaccine.

EXAMPLE 12

An attenuated mumps virus strain which was prepared for 15 serial passages according to Example 3 was further propagated for 5-20 serial passages as in Example 1 using amnions, thereby being adapted to an amnion of an embryonated hen's egg. It became feasible to use an amnion of an embryonated hen's egg as a culture host to obtain an attenuated virus for vaccine in high yields. This mumps virus was used as a seed and inoculated into an amniotic cavity of an embryonated hen's egg as in Example 4 and then cultivated at 34°-35° C. for 5-6 days. After addition of a suitable stabilizer to a vaccine fluid containing viruses purified from the amniotic fluid, the vaccine fluid was divided into a plurality of small containers, and lyophilized for a dried vaccine.

EXAMPLE 13

An attenuated mumps virus strain which was prepared for 15 serial passages according to Example 3 was further propagated for 5-20 serial passages as in Example 2 using quail embryo fibroblast cells, thereby being adapted to a quail embryo fibroblast cell. It became feasible to use a quail embryo fibroblast cell as a culture host to obtain an attenuated virus for vaccine in high yields. This mumps virus was used as a seed and inoculated in a quail embryo fibroblast cell as in Example 5 and then cultivated at 33°-36° C. for 4-7 days. After addition of a suitable stabilizer to the culture medium centrifuged as in Example 4, the vaccine fulid was divided into a plurality of small containers, and lyophilized for a dried vaccine.

EXAMPLE 14

An attenuated mumps virus strain which was prepared for 15 serial passages according to Example 3 was further inoculated in WI-38 cells and cultivated at 35°-39° C. for 4-7 days as in Example 6. After addition of a suitable stabilizer to the culture medium centrifuged as in Example 4, the vaccine fluid was divided into a plurality of small containers, the lyophilized for a dried vaccine.

EXAMPLE 15

An attenuated mumps virus strain which was prepared for 15 serial passages according to Example 3 was inoculated into MRC-5 cells and cultivated at 35°-39° C. for 4-7 days as in Example 6. After addition of a suitable stabilizer to the culture medium centrifuged as in Example 4, the vaccine fluid was divided into a plurality of small containers, and lyophilized for a dried vaccine.

EXPERIMENT I

The vaccines prepared in Examples 4 to 15 were examined. Each of the vaccines was injected by intracerebral routes into cynomolgus monkey (Macaca irus) to examine clinical reaction, pathological findings and immune response. The vaccine was given to each monkey by injection of 0.5 ml into the thalamic region of each hemisphere and by injection of 0.25 ml into the cerebellomedullary cistern. Thereafter, the monkeys treated were observed for 21 days. The results are shown in Table I. No abnormal symptoms were found and a remarkable antibody response was observed for all the vaccines.

TABLE I

| Vaccine Example No. | Virus inoculum* | Number of Monkeys injected | Clinical reaction | Pathological findings | Seroconversion ratio** | Average neutralization antibody titre in sera |
|---|---|---|---|---|---|---|
| 4 | $10^{6.0}$ | 10 | none | normal | 10/10 (100%) | $2^{5.5}$ |
| 5 | $10^{6.0}$ | 10 | none | normal | 10/10 (100%) | $2^{5.3}$ |
| 6 | $10^{5.5}$ | 10 | none | normal | 10/10 (100%) | $2^{5.0}$ |
| 7 | $10^{5.6}$ | 10 | none | normal | 10/10 (100%) | $2^{5.0}$ |
| 8 | $10^{6.0}$ | 10 | none | normal | 10/10 (100%) | $2^{4.8}$ |
| 9 | $10^{5.9}$ | 10 | none | normal | 10/10 (100%) | $2^{5.4}$ |
| 10 | $10^{6.0}$ | 10 | none | normal | 10/10 (100%) | $2^{5.0}$ |
| 11 | $10^{5.7}$ | 10 | none | normal | 10/10 (100%) | $2^{5.3}$ |

TABLE I-continued

| Vaccine Example No. | Virus inoculum* | Number of Monkeys injected | Clinical reaction | Pathological findings | Sero-conversion ratio** | Average neutralization antibody titre in sera |
|---|---|---|---|---|---|---|
| 12 | $10^{5.9}$ | 10 | none | normal | 10/10 (100%) | $2^{5.4}$ |
| 13 | $10^{6.0}$ | 10 | none | normal | 10/10 (100%) | $2^{5.0}$ |
| 14 | $10^{5.8}$ | 10 | none | normal | 10/10 (100%) | $2^{5.3}$ |
| 15 | $10^{5.7}$ | 10 | none | normal | 10/10 (100%) | $2^{4.9}$ |

*$TCID_{50}$ (50% tissue culture infective dose)
**number of monkeys converted positive/number of monkeys injected It was found that the mumps virus vaccines of Examples 4-15 are properly attenuated, safe and effective.

EXPERIMENT II

Various tests were carried out for each vaccine of Examples 4, 5, 6 and 7 according to the U.S. Official standard (Federal Register, Vol. 33, No. 14, 1968). In the case of the vaccines of Examples 6 and 7 in which human diploid cells were used as a virus culture host, additional assays were carried out according to W.H.O. Requirement for Biological Substances, No. 7 (revised in 1971). After it was confirmed that the vaccines passed these standards, the vaccines were subcutaneously injected into children 1-10 years old, who had no antibody against mumps. The results of this field test are shown in Table II.

TABLE II

| Vaccine Example No. | Virus inoculum* | Number of children injected | Clinical reaction** | Sero-conversion ratio*** | Average neutralization antibody titre in sera |
|---|---|---|---|---|---|
| 4 | $10^{5.6}$ | 3590 | none | 1234/1297 (95.14%) | $2^{3.88}$ |
| 5 | $10^{5.5}$ | 30 | none | 24/25 (96%) | $2^{3.7}$ |
| 6 | $10^{5.1}$ | 30 | none | 19/20 (95%) | $2^{4.0}$ |
| 7 | $10^{5.2}$ | 30 | none | 29/29 (100%) | $2^{4.1}$ |

*$TCID_{50}$ (50% tissue culture infective dose)
**fever (37.5° C.$\leq$) and parotid swelling
***number of children converted positive/number of children injected As seen from Table II, no abnormal clinical reaction was observed for all the vaccines. The vaccines prepared according to this invention are at least equal in effectiveness to vaccines prepared according to the prior processes, have stronger immunogenecity and are safe.

What is claimed is:

1. A method of preparing a live attenuated mumps virus for a vaccine comprising:
   incubating a wild mumps virus strain in a living cell selected from the group consisting of embryonated hen's egg chorio-allantoic membrane, chick embryo fibroblast and human diploid cell for 1-18 passages sufficient to attenuate the virus, and
   subjecting the thus attenuated virus to successive cultivation in a living cell selected from the group consisting of embryonated hen's egg amnion, embryonated hen's egg chorio-allantoic membrane and human diploid cell to propagate the virus.

2. A method according to claim 1 wherein the second cell is embryonated hen's egg amnion.

3. A method according to claim 1 wherein the virus is attenuated through 8-14 serial passages.

4. A method according to claim 1 wherein the attenuation of virus includes the steps of
   inoculating the virus into an amniotic cavity,
   cultivating the virus for 5-6 days, and
   harvesting the amniotic fluid, from which the attenuated virus is obtained.

5. A method according to claim 4 wherein the attenuation is carried out for 8-14 serial passages.

6. A method according to claim 1 wherein the second cell is embryonated hen's egg amnion, and the propagation of virus includes the steps of inoculating the virus into an amniotic cavity, cultivating the virus for 5-6 days, and harvesting the amniotic fluid, from which the propagated virus is obtained.

7. A method of preparing a live attenuated mumps virus for a vaccine comprising:
   incubating a wild mumps virus strain in a living cell selected from the group consisting of embryonated hen's egg chorio-allantoic membrane, chick embryo fibroblast and human diploid cell for 1-18 passages sufficient to attenuate the virus; and
   subjecting the thus attenuated virus to successive cultivation in a living human diploid cell to propagate the virus.

8. A method of preparing a live attenuated mumps virus for a vaccine comprising:
   incubating a wild mumps virus strain in a living human diploid cell for 1-18 serial passages sufficient to attenuate the virus; and
   subjecting the thus attenuated virus to successive cultivation in a living cell selected from the group consisting of embryonated hen's egg amnion, embryonated hen's egg chorio-allantoic membrane and human diploid cell to propagate the virus.

* * * * *